United States Patent
Ichikawa et al.

(10) Patent No.: US 7,406,858 B2
(45) Date of Patent: Aug. 5, 2008

(54) SCIENTIFIC PHENOMENA EVALUATION DEVICE, DIFFUSION VELOCITY MEASUREMENT EXPERIMENTAL DEVICE, AND MANUFACTURING METHOD OF THE DEVICE

(75) Inventors: Yasunori Ichikawa, Minami-Ashigara (JP); Tomohide Ueyama, Minami-Ashigara (JP); Fumiko Shiraishi, Minami-Ashigara (JP); Akira Kato, Minami-Ashigara (JP)

(73) Assignee: FUJIFILM Corporation, Tokyo (JP)

(*) Notice: Subject to any disclaimer, the term of this patent is extended or adjusted under 35 U.S.C. 154(b) by 379 days.

(21) Appl. No.: 11/059,344

(22) Filed: Feb. 17, 2005

(65) Prior Publication Data

US 2005/0183495 A1 Aug. 25, 2005

(30) Foreign Application Priority Data

Feb. 20, 2004 (JP) .............................. 2004-045315

(51) Int. Cl.
*G01N 11/00* (2006.01)
(52) U.S. Cl. .................................... 73/53.01
(58) Field of Classification Search ................ 73/53.01, 73/290 R, 323, 290 B
See application file for complete search history.

(56) References Cited

U.S. PATENT DOCUMENTS

| | | | |
|---|---|---|---|
| 6,197,575 B1 * | 3/2001 | Griffith et al. | 435/288.4 |
| 6,719,682 B2 * | 4/2004 | Kellogg et al. | 494/84 |
| 2004/0203136 A1 * | 10/2004 | Kellogg et al. | 435/287.2 |

FOREIGN PATENT DOCUMENTS

JP 2000-242162 A 9/2000

* cited by examiner

*Primary Examiner*—Hezron Williams
*Assistant Examiner*—Rodney Frank
(74) *Attorney, Agent, or Firm*—Sughrue Mion, PLLC

(57) ABSTRACT

According to the present invention, a continuous layer liquid used as a continuous layer of a diffusion phenomenon is injected into the first reservoir, and passed through the channels to the second reservoirs to fill the plurality of radially formed channels with the continuous layer liquid. Then, a predetermined amount of diffusion experiment reagent, for example, a coloring liquid used as a diffusion substance of the diffusion phenomenon is injected into the first reservoir. This causes the diffusion experiment reagent to be diffused from the first reservoir to the second reservoirs only by the diffusion phenomenon. At this time, the radially formed channels have the different sectional areas, and thus the diffusion experiment reagent is diffused through the channels at different velocities. This allows the diffusion phenomena that occur in the micro channels or the diffusion velocities to be observed or measured with ease using an inexpensive device.

35 Claims, 3 Drawing Sheets

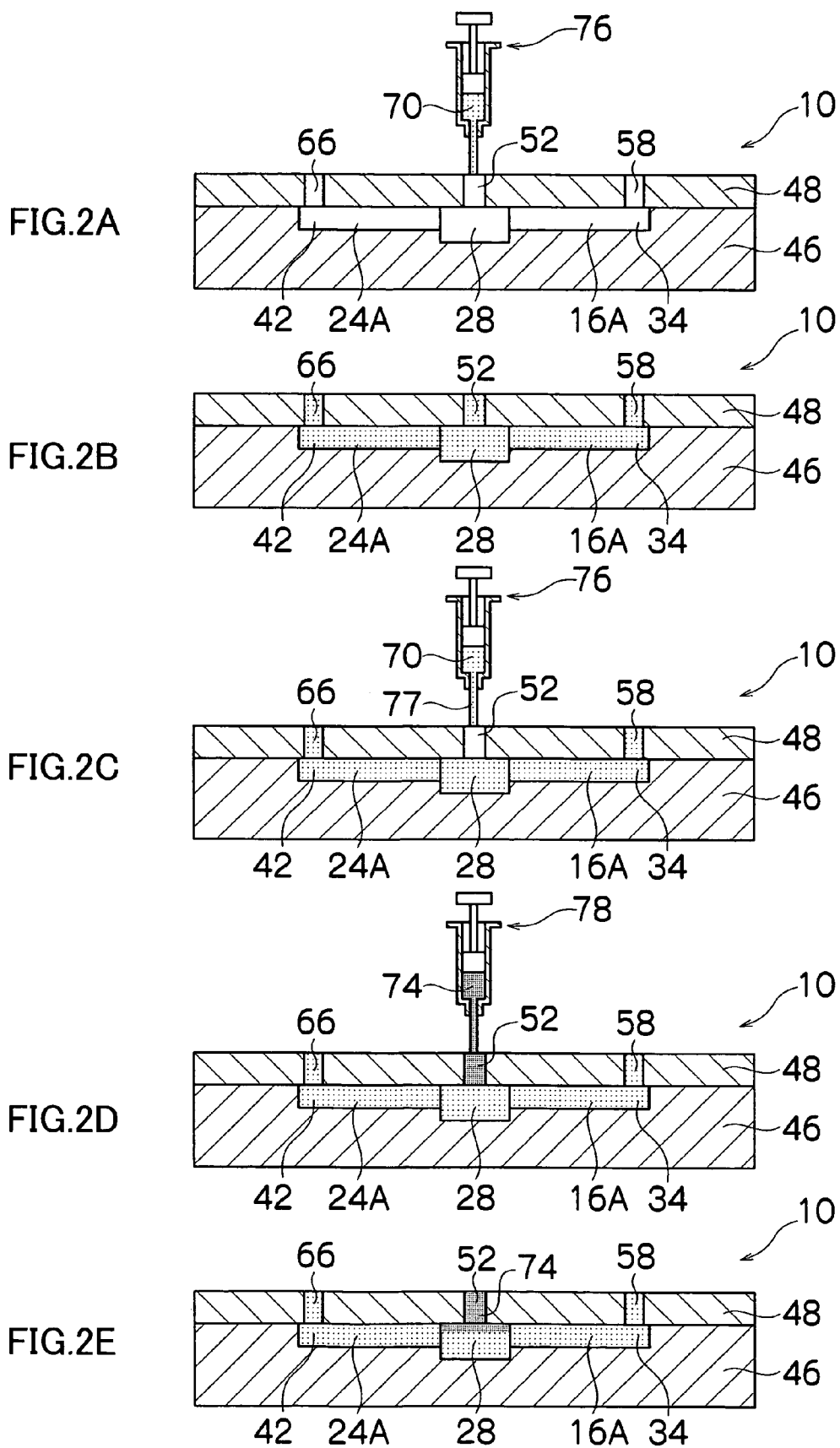

SCIENTIFIC PHENOMENA EVALUATION DEVICE, DIFFUSION VELOCITY MEASUREMENT EXPERIMENTAL DEVICE, AND MANUFACTURING METHOD OF THE DEVICE

BACKGROUND OF THE INVENTION

1. Field of the Invention

The present invention relates to a scientific phenomena evaluation device, a diffusion velocity measurement experimental device, and a manufacturing method thereof, and more particularly to a scientific phenomena evaluation device, a diffusion velocity measurement experimental device, and a manufacturing method thereof that are inexpensive, environmentally friendly, and appropriate for enjoying high technology with ease.

2. Description of the Related Art

Various types of scientific phenomena evaluation devices such as scientific experiment education materials have been proposed (see Japanese Patent Application Laid-open No. 2000-242162).

Japanese Patent Application Laid-open No. 2000-242162 discloses a science education material that allows observation of natural phenomena by temperature changes of water by cooling or freezing water vapor in the air or water or water vapor in a container, is small in size and simple in structure, and is capable of faithfully reproducing various kinds of natural phenomena by temperature changes of water.

As scientific experimental devices for education, experimental kits such as "Science and Learning: Experimental Kit Series" and "Scientific Global Environment Analysis Kit for Adults" are available from Gakken Co., Ltd. Such experimental kits, which provide dream to children or enjoyment of experiments to users, are available at relatively low prices of about a few hundred yen to three thousand yen and well received.

SUMMARY OF THE INVENTION

However, such a conventional scientific phenomena evaluation device as described in Japanese Patent Application Laid-open No. 2000-242162 has a relatively complex configuration and is not available at low price, and is thus inappropriate for all students in the class to buy.

On the other hand, experimental kits having relatively simple configurations are often available at relatively low prices, and appropriate for all students in the class to buy. However, such kits have poor finishing accuracy and use a large amount of chemicals, and if all students in the class use the kits, it is environmentally unfriendly in terms of wastewater treatment or the like and undesirable.

Also, such conventional experimental kits provide experience of classical scientific experiments, and an extremely limited number of kits provide enjoyment of high technology with ease. Particularly, high technology such as microtechnology or nanotechnology has been recently noted, and experiment education materials are required that allow observation with ease of diffusion phenomena of substances that occur in micro channels that are minute channels. Further, it is desirable to conveniently carry the experiment education materials and measure diffusion velocity of the substances that occur in the micro channels with ease.

The invention is achieved in view of such circumstances, and has an object to provide a scientific phenomena evaluation device, a diffusion velocity measurement experimental device, and a manufacturing method thereof that are inexpensive, environmentally friendly, and appropriate for enjoying high technology including diffusion phenomena with ease.

In order to achieve the above described object, a first aspect of the present invention provides a scientific phenomena evaluation device, comprising: a first reservoir, a plurality of second reservoirs formed around the first reservoir, and a plurality of channels for communicating the first reservoir and each of the plurality of second reservoirs, wherein the first reservoir and the plurality of second reservoirs communicate with each other radially through the plurality of channels, the plurality of channels are minute channels having different sectional areas of 1 $mm^2$ or less, and scientific phenomena in the channels are visually perceivable.

According to the first aspect, a continuous layer liquid used as a continuous layer of a diffusion phenomenon is injected into the first reservoir, and passed through the channels to the second reservoirs to fill the plurality of radially formed channels with the continuous layer liquid. Then, a predetermined amount of diffusion experiment reagent, for example, a coloring liquid used as a diffusion substance of the diffusion phenomenon is injected into the first reservoir. This causes the diffusion experiment reagent to be diffused from the first reservoir to the second reservoirs only by the diffusion phenomenon. At this time, the radially formed channels have the different sectional areas, and thus the diffusion experiment reagent is diffused through the channels at different velocities. This allows the diffusion phenomena of the substance that occur in the micro channels or the diffusion velocities to be observed or measured with ease using an inexpensive device. Besides the simple observation of the diffusion phenomena, the evaluation device according to the invention can evaluate various phenomena of various kinds of high technology caused by diffusion of a substance through a liquid, such as a heat transfer phenomenon of a liquid, a mixing phenomenon of a liquid, or a chemical reaction of a liquid (for example, an acid/alkali reaction or a hydrolysis reaction).

The reservoir is usually hollow, and chemicals are supplied into the reservoir when the evaluation device is operated.

In the evaluation device, the radially formed channels are the minute channels having the sectional areas of 1 $mm^2$ or less, and thus the evaluation device provides adequate accuracy for experiencing high technology, and uses a small amount of continuous layer liquid or diffusion experiment reagent to be environmentally friendly.

In the first aspect, it is preferable that lengths of the channels are equal and the sectional areas of the channels are different at a fixed ratio. This causes capacities of the channels to be also different at a fixed ratio. This is because the capacities of the channels are associated with quantification of the diffusion velocity, and setting the capacities at the fixed ratio facilitates the quantification of the diffusion velocity. Thus, in the invention, the radially formed channels have the different sectional areas, and with reference to a channel having a maximum sectional area among the channels, sectional areas of other channels are reduced at the fixed ratio. In this case, the sectional area of the channel having the maximum sectional area is 1 $mm^2$ of less as described above, preferably 0.0025 to 0.64 $mm^2$, and more preferably 0.01 to 0.25 $mm^2$. The capacities of the first reservoir and the second reservoir are preferably 5 to 5000 $mm^3$.

In the first aspect, graduations indicating a diffusion distance are preferably provided along each channel. These graduations clearly show diffusion distances of the substance through the channels having the different sectional areas.

The evaluation device according to the first aspect of the present invention preferably includes: a base plate in which a plurality of radially extending long grooves, the first reservoir, and the second reservoirs are formed; and a cover plate bonded to a surface of the base plate and cover the long grooves to form the plurality of radial channels in the base plate, the base plate and/or the cover plate being transparent. The evaluation device including the base plate and the cover plate is easy to make, and the transparent base plate and/or cover plate allows scientific phenomena in the radial channels to be visually perceived.

Preferably, through-holes that allow communication between the first and second reservoirs and outside air are formed in the cover plate. Such through-holes that allow communication between the first and second reservoirs and the outside air may be used as an inlet of a liquid into the radial channels or air vents, and facilitate control of the phenomena that occur in the micro channels.

In order to achieve the above described object, a second aspect of the present invention provides a diffusion velocity measurement experimental device, wherein the device is a portable experimental device for measuring diffusion velocity of a substance by the scientific phenomena evaluation device of the first aspect.

The evaluation device according to the first aspect of the present invention may be effectively used as the diffusion velocity measurement experimental device.

In order to achieve the above described object, a third aspect of the present invention provides a manufacturing method of the scientific phenomena evaluation device of the first aspect, comprising the steps of: applying a resin material to a surface of an inverted mold in which inverted shapes of long grooves in a base plate are formed, curing the resin material, and releasing the cured resin material from the inverted mold to form the base plate.

In order to achieve the above described object, a fourth aspect of the present invention provides a manufacturing method of the diffusion velocity measurement experimental device of the second aspect, comprising the steps of: applying a resin material to a surface of an inverted mold in which inverted shapes of long grooves in a base plate are formed, curing the resin material, and releasing the cured resin material from the inverted mold to form the base plate.

According to the third and the fourth aspect, the inverted mold having the surface in which the inverted shapes of the long grooves are formed is used to form the base plate by transfer molding, thereby providing a base plate with accuracy at low price and providing an inexpensive evaluation device. It is described that "a resin material is applied to a surface of an inverted mold . . . , the resin material is cured", but a method of bringing a resin film into contact with a surface of an inverted mold and transferring a shape of long grooves to a surface of the resin material by hot pressing or the like is based on the same technical idea and falls within the equivalent scope of the invention.

As described above, the invention provides enjoyment of high technology with ease at low price in an environmentally friendly manner.

BRIEF DESCRIPTION OF THE DRAWINGS

FIGS. 2A to 2E are conceptual sectional views of a procedure of diffusion velocity measurement.

DETAILED DESCRIPTION OF THE PREFERRED EMBODIMENTS

Now, a preferred embodiment of a scientific phenomena evaluation device, a diffusion velocity measurement experimental device, and a manufacturing method thereof will be described in detail with reference to the accompanying drawings.

Figure 1A:
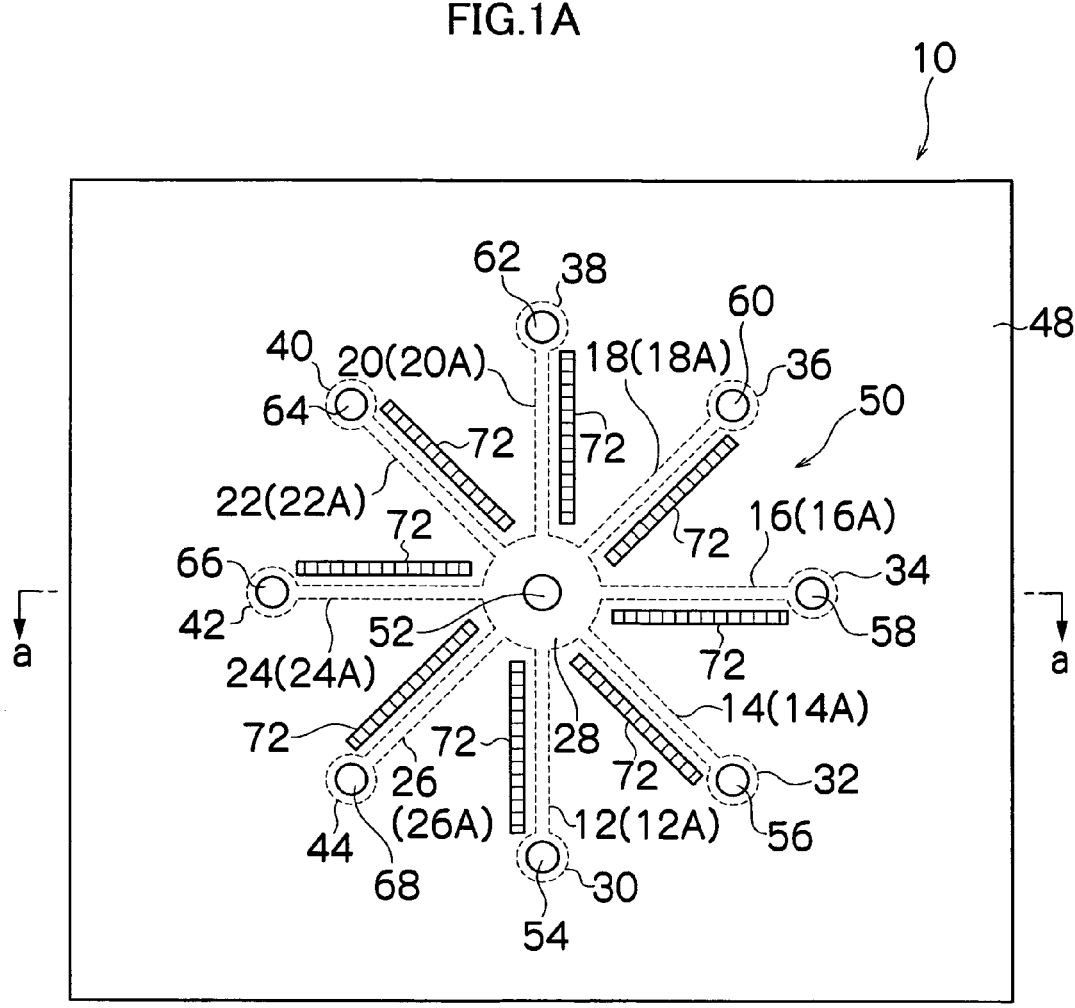
FIGS. 1A and 1B are a plan view and a conceptual sectional view of a configuration of a diffusion velocity measurement experimental device according to the invention.
Figure 1B:
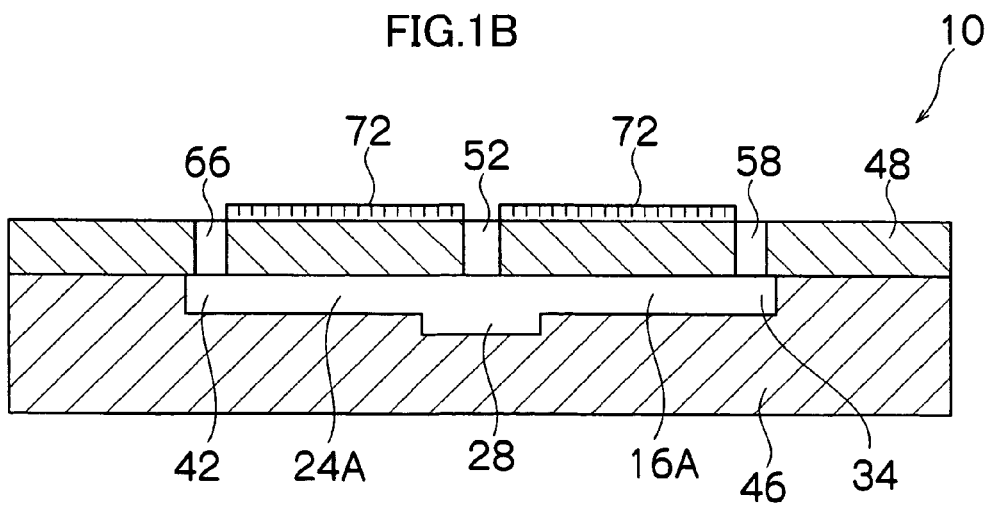

FIG. 1A is a plan view of a configuration of a diffusion velocity measurement experimental device 10 as a preferable aspect of the scientific phenomena evaluation device according to the invention. FIG. 1B is a sectional view taken along the line a-a in FIG. 1A.

The diffusion velocity measurement experimental device 10 mainly includes: a base plate 46 in which a plurality of (eight in FIG. 1) radially extending long grooves 12 to 26, a first reservoir 28, and a plurality of second reservoirs 30 to 44 are formed; and a cover plate 48 bonded to a surface of the base plate 46 and cover the long grooves 12 to 26 to form radial channels 12A to 26A in the base plate 46. In the description below, an example of eight channels as the plurality of radially formed channels 12A to 26A is described, but the number of the channels is not limited to eight, and may be three or more.

Specifically, the eight channels 12A to 26A radially extend from the first reservoir 28 and are connected to the second reservoirs 30 to 44 respectively, thereby forming a radial channel 50 consisting of the eight channels 12A to 26A. The eight channels 12A to 26A are minute channels having different sectional areas of 1 $mm^2$ or less. In this case, it is preferable that the eight channels 12A to 26A have the same length, and the sectional areas of the eight channels 12A to 26A are different at a fixed ratio. For example, the eight channels 12A to 26A have the length of 20 mm to 40 mm and different sectional areas of 1 $mm^2$, 0.9 $mm^2$, 0.8 $mm^2$, 0.7 $mm^2$, 0.6 $mm^2$, 0.5 $mm^2$, 0.4 $mm^2$, 0.3 $mm^2$ in decrements of 0.1 $mm^2$. Specifically, with reference to a sectional area of a channel having a maximum sectional area, sectional areas of other seven channels are reduced by a fixed ratio of 10%. The sectional area of the channel having the maximum sectional area may be 1 $m^2$ or less, and the fixed ratio of reduction of the sectional area may be other than 10%. Capacities of the first reservoir 28 and the second reservoirs 30 to 44 are preferably 5 to 5000 $mm^3$.

Further, a first through-hole 52 that can communicate with outside air is formed in a portion of the cover plate 48 corresponding to the first reservoir 28, and a plurality of second through-holes 54 to 68 that can communicate with outside air are also formed in portions of the cover plate 48 corresponding to the second reservoirs 30 to 44. The first through-hole 52 may be used as an inlet for introducing a continuous layer liquid 70 (see FIG. 2) used as a continuous layer of a diffusion phenomenon into the first reservoir 28, and the second through-holes 54 to 68 may be used as air vents for venting air in the channels 12A to 26A when the channels 12A to 26A are filled with the continuous layer liquid 70 injected into the first reservoir 28. Graduations 72 are provided along the channels 12A to 26A on the surface of the cover plate 48. The graduations 72 may be carved in the surface of the cover plate 48 or a scale with the graduations 72 may be attached to the surface of the cover plate 48.

Sizes of planes of the base plate 46 and the cover plate 48 for making the diffusion velocity measurement experimental device 10 are not limited, but the planes may be of a portable size of, for example, 100×100 mm in view of the nature of the diffusion velocity measurement experimental device 10 used at school. Thicknesses of the base plate 46 and the cover plate 48 are not limited but may be, for example, about 5 mm in view of strength, cost efficiency, or the like.

A material of the base plate 46 is not limited, but resin materials, more specifically, polydimethyl sulfoxide (PDMS), polymethylmethacrylate (PMMA), polyvinyl chloride (PVC), ultraviolet curable resin, thermoset resin, polycarbonate (PC) or the like may be preferably used in terms of facilitating a below described manufacturing method.

A sectional shape of each of the long grooves 12 to 26 formed in the base plate 46 is not limited, but may be selected from various kinds of shapes such as a rectangular shape (a square or a rectangle), a trapezoidal shape, a V shape, or a semicircular shape. The rectangular shape (the square or the rectangle) is preferable in terms of facilitating the below described manufacturing method.

A material of the cover plate 48 is not limited, but the cover plate 48 is preferably transparent in order to allow scientific phenomena in the radial channels 12A to 26A to be visually perceived. As such a material, various types of resin plates, more specifically, polydimethyl sulfoxide (PDMS), polymethylmethacrylate (PMMA), polyvinyl chloride (PVC), and ultraviolet curable resin, polycarbonate (PC), or the like, various types of resin films, more specifically, polyethylene terephthalate (PET), polyethylene naphthalate (PEN), and triacetyl cellulose (TAC), or the like, and various types of glass (soda lime glass, borosilicate glass, or the like) may be used.

The cover plate 48 is generally a flat plate having flat front and back surfaces, but may have a configuration such that a front surface at portions corresponding to the minute radial channels 12A to 26A may be formed into semi-cylindrical convex lens shapes to allow observation in an enlarged state.

Such a configuration that the cover plate 48 is opaque and the base plate 46 is transparent may be used.

Ensuring sufficient flatness of a front surface of the base plate 46 (a surface in which the long grooves are formed) and a back surface of the cover plate 48 (a surface bonded to the base plate 46) is preferable in terms of forming the radial channel 50 and preventing leak.

Next, a forming method of the base plate 46 will be described. First, an inverted mold is prepared having a surface in which inverted shapes of the long grooves 12 to 26 in the base plate 46 are formed. In the surface of the inverted mold, inverted shapes of the first reservoir 28 and the second reservoirs 30 to 44 need to be further formed. As a manufacturing method of the inverted mold, various types of known machining methods may be used such as machining by a machining center or the like, electrical discharge machining, ultrasonic machining, or photoetching.

Then, a release agent is applied to the surface of the inverted mold. An appropriate release agent may be used depending on a type or a machining condition (a temperature or the like) of a resin material for the base plate 46.

Next, the resin material is applied to the surface of the inverted mold and cured. When the resin material is an ultraviolet curable resin, the applied resin material is irradiated with ultraviolet light and cured. When the resin material is a thermoset resin such as polyvinyl chloride (PVC), the resin material is brought into contact with the surface of the inverted mold and heat transfer molded by a hot pressing machine.

Then, the cured resin material is released from the inverted mold.

Such a method allows the long grooves 12 to 26 to be formed with accuracy at low price, thereby providing an inexpensive evaluation device.

Next, a using method of the diffusion velocity measurement experimental device 10 according to the invention will be described. For the diffusion velocity measurement experimental device 10, the following members 1) to 12) need to be provided as a set.

1) The inverted mold
2) The resin material for the base plate 46
3) A frame for forming the base plate 46 (used as a frame when the resin is poured in forming the base plate 46)
4) The cover plate 48
5) A syringe for a liquid (used for injecting necessary liquids into the first reservoir 28 depending on test purposes. A syringe exclusive to each chemical to be injected may be prepared, or one syringe may be cleaned and reused.) An injection tool such as a dropper may be used instead of the syringe for supplying liquids into the reservoir in view of the low price and safety for school education materials, but an example of the syringe will be described below.
6) A sealing tape for the first through-hole 52 (which serves as a lid of the first reservoir 28 that is a supply hall of chemicals, and is for closing the first reservoir 28 after the chemicals are supplied into the first reservoir 28. The tape may be used as a lid for the second reservoirs 30 to 44.)
7) A needle (for boring an air vent in the sealing tape)
8) A casing (mounted for preventing leak from between the cover plate 48 and the base plate 46 or preventing damage to the cover plate 48 or the like when the experimental set is assembled. Various functions for experimental purposes, for example, a magnifying glass or the like for facilitating observation of the channels may be mounted to the casing.)
9) A feeding device A feeding device using volume expansion of a liquid and/or a gas in the first reservoir 28 may be used instead of the device that feeds the liquid using the principle of a pump such as the syringe or the dropper. The feeding device using the volume expansion is a feeding device using a phenomenon such that applying heat to the first reservoir 28 with the first reservoir 28 being closed by the sealing tape (placing a fingertip on the tape and heating the tape by body heat, or the like) causes the volume expansion of the liquid and/or the gas in the first reservoir 28.

10) Chemicals used in measurement of diffusion velocity

The chemicals are the continuous layer liquid 70 used as the continuous layer of the diffusion phenomenon or a diffusion experiment reagent 74 (see FIG. 2) used as a diffusion substance.

11) An experiment guide

A guide of events that can be learned by this set describing a purpose of diffusion velocity measurement conducted using the set, explanation on the phenomena, applications, or the like is attached if required.

12) An experimental method procedure manual

This set is adapted for students to make the base plate 46 by hand, but if the step of making the base plate 46 by hand is omitted, a completed base plate 46 may replace 1) to 3).

Next, details of the diffusion velocity measurement experiment using the set of the diffusion velocity measurement experimental device 10 will be described.

FIGS. 2A to 2E are conceptual sectional views of a procedure of the experimental method.

As shown in FIG. 2A, an injection port of a syringe 76 is connected to the first through-hole 52. Then, as shown in FIG. 2B, the syringe 76 is used to inject the continuous layer liquid 70 used as the continuous layer of the diffusion phenomenon into the first reservoir 28 to fill the radially formed channels 12A to 26A with the continuous layer liquid 70.

In injecting the continuous layer liquid 70, the continuous layer liquid 70 is first injected to an inlet level of the first through-hole 52 above the first reservoir 28, and air is removed from the first reservoir 28 and first through-hole 52. Then, the syringe 76 is once released from the first through-hole 52 and set so that the injection port of the syringe 76 tightly fits the inlet of the first through-hole 52, and the continuous layer liquid 70 in the syringe 76 is injected again. This causes the continuous layer liquid 70 to pass through the channels in a descending order of sectional area by a pressure of the syringe 76, and the continuous layer liquid 70 is accumulated in the second reservoirs 30 to 44. In this case, the second through-holes 54 to 68 that provides communication between the second reservoirs 30 to 44 and the outside air are opened, or the needle is used to bore air vents in sealing tapes if the sealing tapes are attached to inlets of the second through-holes 54 to 68. This injecting operation is performed for each of the eight channels 12A to 26A, and when all the radially formed channels 12A to 26A are filled with the continuous layer liquid 70, the syringe 76 is released from the first through-hole 52.

Next, as shown in FIG. 2C, a needle 77 is fitted to the injection port of the syringe 76 to draw the continuous layer liquid 70 accumulated in the first through-hole 52 and the first reservoir 28 to a liquid level where no air is introduced into the channels 12A to 26A. This is to ensure an injecting space for the diffusion experiment reagent 74 to be next injected into the first reservoir 28. FIG. 2C shows a state where the continuous layer liquid 70 in the first through-hole 52 only is drawn, but the continuous layer liquid 70 in the first reservoir 28 may be drawn partway.

Then, as shown in FIG. 2D, another syringe 78 is used to inject a predetermined amount (for example, 1 cc) of diffusion experiment reagent 74 into the first reservoir 28. FIG. 2D shows a state where the diffusion experiment reagent 74 is injected into the first reservoir 28 until the first through-hole 52 is filled correspondingly to FIG. 2C.

This causes the diffusion experiment reagent 74 to be diffused through the channels 12A to 26A as shown in FIG. 2E. The diffusion experiment reagent 74 is preferably colored (a dye, a pigment, or other coloring liquids). When the diffusion experiment reagent 74 is not colored, for example, when diffusion velocity of acid or alkali is measured, it is preferable that a pH indicator is previously added to the continuous layer liquid 70 to be injected into the channels 12A to 26A to allow changes of color by diffusion of acid or alkali to be checked. Then, a timer is activated when the diffusion experiment reagent 74 is injected, and a time is measured required for diffusion through a channel having a minimum capacity (the same as a channel having a minimum sectional area) to reach a tip of the channel. A diffusion distance is also measured by the graduations indicating along each of the channels 12A to 26A where diffusion through each of other channels reaches at that timing. Based on data thus obtained, diffusion velocity through each channel is calculated from the capacity of each channel, the capacity of the first reservoir, an injection amount of the diffusion experiment reagent 74, or the like.

In FIGS. 1 to 2, the continuous layer liquid 70 is fed from the first reservoir 28 to the second reservoirs 30 to 44 using the principle of the pump of the syringe 76, but may be fed using the volume expansion of the liquid and/or the gas in the first reservoir 28 as shown in FIGS. 3A to D. FIG. 3 shows a state where the first reservoir 28 is formed in the cover plate 48 with the first through-hole 52 being omitted. When the continuous layer liquid 70 is fed using the volume expansion of the liquid and/or the gas in the first reservoir 28, the capacity of the first reservoir is preferably 100 to 5000 mm$^3$ larger than 5 to 5000 mm$^3$ described above.

Figure 3A:
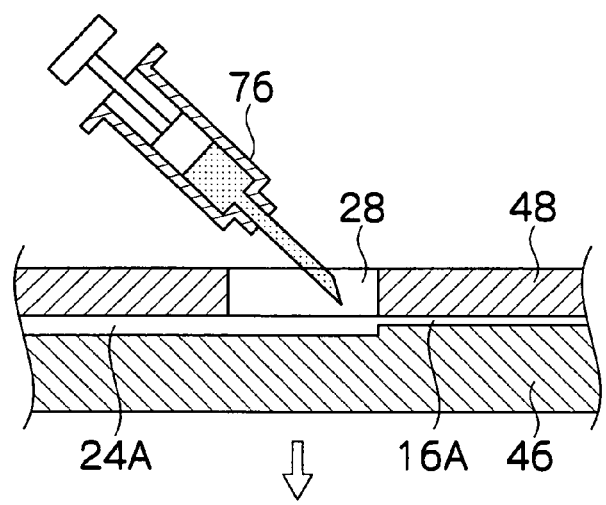
FIGS. 3A to 3D illustrate a case where a continuous layer liquid is supplied from a first reservoir to second reservoirs using volume expansion of a liquid and/or a gas.
Figure 3B:
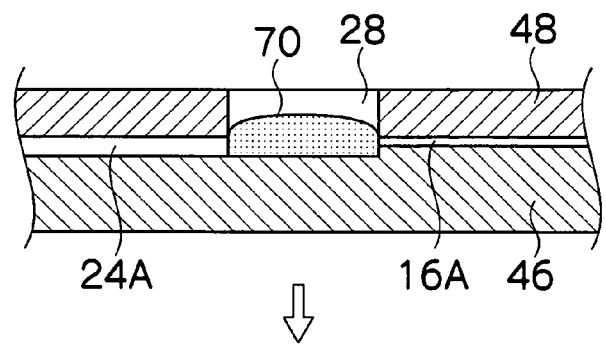
Figure 3C:
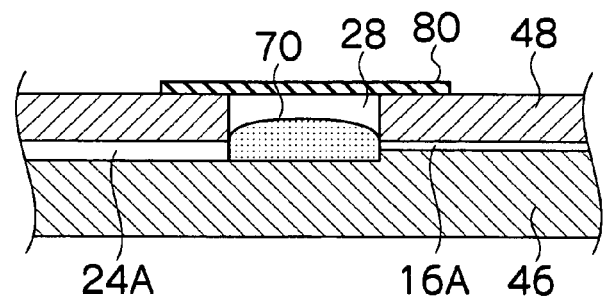
Figure 3D:
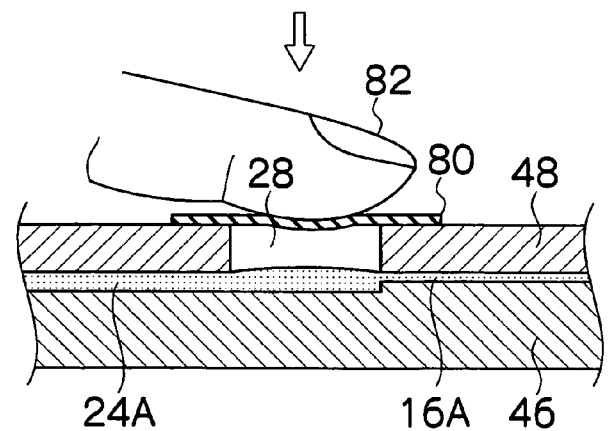

As shown in FIGS. 3A and 3B, for example, the syringe 76 is used to inject the continuous layer liquid 70 into the first reservoir 28. Then, as shown in FIG. 3C, a surface of the first reservoir 28 is sealed by a sealing tape 80 to close the first reservoir 28. The sealing tape 80 is coated with an adhesive material on one surface (a lower surface in the drawing) and seals the first reservoir 28 from the outside air. Then, as shown in FIG. 3D, a fingertip 82 is placed on the sealing tape 80. This causes a feeding device to be formed in the first reservoir 28. This feeding device operates such that the heat of the fingertip 82 causes the volume expansion of the liquid and/or the gas in the first reservoir 28 to feed the continuous layer liquid 70 into the second reservoirs 30 to 44 through the radial channels 12A to 26A.

In a configuration similar to the configuration in 3D, the feeding device may operate such that the sealing tape 80 is pushed by the fingertip 82 and bent downward to reduce the capacity of the first reservoir 28, thereby feeding the continuous layer liquid 70 into the radial channels.

In order to facilitate observation of such phenomena, a hand lens or a magnifying glass may be used. The cover plate 48 at the portions corresponding to the radial channels 12A to 26A may have a magnifying glass function (a lens function) as descried above.

The diffusion velocity measurement experimental device 10 described above includes important parts that are simplified as much as possible and inexpensive, and allows experiments with high accuracy in order for children to conduct scientific experiments in microworld with enjoyment and dream. The diffusion velocity measurement experimental device 10 also allows measurement of diffusion velocity by a portable small device. Diffusion velocity measurement experiments can be conducted with an extremely small amount of reagents, thereby reducing wastewater or wastes after the experiments to be environmentally friendly. Further, the radial channels 12A to 26A are the minute channels in micro scales, and a test device using microtechnology or nanotechnology can be experienced.

In the embodiment, the diffusion velocity measurement experimental device 10 is described as an example of the scientific phenomena evaluation device, but not limited to the measurement of the diffusion velocity, the evaluation device can evaluate various kinds of chemical or physical phenomena caused by diffusion of a substance through a liquid, such as a heat transfer phenomenon of a liquid, a mixing phenomenon of a liquid, or a chemical reaction of a liquid (for example, an acid/alkali reaction or a hydrolysis reaction).

The radial channels 12A to 26A, the first reservoir 28, and the second reservoirs 30 to 44 are formed in the base plate 46, and the first through-hole 52 and the second through-holes 54 to 68 are formed in the cover plate 48, but other aspects may be possible. For example, the first reservoir 28 may be formed in the cover plate 48 as shown in FIG. 3.

Further, the syringes 76 and 78 are used to supply and draw the liquid into and from the reservoir 28, but a dropper or a micro syringe having the same function may replace the syringe as described above. Generally, an inexpensive dropper is preferably used for a scientific experiment education material. Depending on test purposes, however, the syringe is sometimes preferably used as described above, such as when the liquid is to be supplied into or drawn from the reservoir 28 in an accurate amount as in the diffusion velocity measurement experiment.

What is claimed is:

1. A scientific phenomena evaluation device, comprising:
a first reservoir;
a plurality of second reservoirs formed around the first reservoir; and
a plurality of channels for communicating the first reservoir and each of the plurality of second reservoirs,
wherein the first reservoir and the plurality of second reservoirs communicate with each other radially through the plurality of channels, the plurality of channels are minute channels having different sectional areas of 1 mm$^2$ or less, and scientific phenomena in the channels are visually perceivable.

2. The scientific phenomena evaluation device according to claim 1, wherein lengths of the channels are equal and the sectional areas of the channels are different at a fixed ratio.

3. The scientific phenomena evaluation device according to claim 1, wherein graduations indicating a diffusion distance are provided along each channel.

4. The scientific phenomena evaluation device according to claim 2, wherein graduations indicating a diffusion distance are provided along each channel.

5. The scientific phenomena evaluation device according to claim 1, further comprising:
a base plate in which a plurality of radially extending long grooves, the first reservoir, and the second reservoirs are formed; and
a cover plate bonded to a surface of the base plate and cover the long grooves to form the plurality of radial channels in the base plate,
wherein the base plate and/or the cover plate being transparent.

6. The scientific phenomena evaluation device according to claim 2, further comprising:
a base plate in which a plurality of radially extending long grooves, the first reservoir, and the second reservoirs are formed; and
a cover plate bonded to a surface of the base plate and cover the long grooves to form the plurality of radial channels in the base plate,
wherein the base plate and/or the cover plate being transparent.

7. The scientific phenomena evaluation device according to claim 3, further comprising:
a base plate in which a plurality of radially extending long grooves, the first reservoir, and the second reservoirs are formed; and
a cover plate bonded to a surface of the base plate and cover the long grooves to form the plurality of radial channels in the base plate,
wherein the base plate and/or the cover plate being transparent.

8. The scientific phenomena evaluation device according to claim 4, further comprising:
a base plate in which a plurality of radially extending long grooves, the first reservoir, and the second reservoirs are formed; and
a cover plate bonded to a surface of the base plate and cover the long grooves to form the plurality of radial channels in the base plate,
wherein the base plate and/or the cover plate being transparent.

9. The scientific phenomena evaluation device according to claim 5, wherein through-holes that allow communication between the first and second reservoirs and outside air are formed in the cover plate.

10. The scientific phenomena evaluation device according to claim 6, wherein through-holes that allow communication between the first and second reservoirs and outside air are formed in the cover plate.

11. The scientific phenomena evaluation device according to claim 7, wherein through-holes that allow communication between the first and second reservoirs and outside air are formed in the cover plate.

12. The scientific phenomena evaluation device according to claim 8, wherein through-holes that allow communication between the first and second reservoirs and outside air are formed in the cover plate.

13. A diffusion velocity measurement experimental device, wherein the device is a portable experimental device for measuring diffusion velocity of a substance by the scientific phenomena evaluation device of claim 1.

14. A diffusion velocity measurement experimental device, wherein the device is a portable experimental device for measuring diffusion velocity of a substance by the scientific phenomena evaluation device of claim 2.

15. A diffusion velocity measurement experimental device, wherein the device is a portable experimental device for measuring diffusion velocity of a substance by the scientific phenomena evaluation device of claim 4.

16. A diffusion velocity measurement experimental device, wherein the device is a portable experimental device for measuring diffusion velocity of a substance by the scientific phenomena evaluation device of claim 8.

17. A diffusion velocity measurement experimental device, wherein the device is a portable experimental device for measuring diffusion velocity of a substance by the scientific phenomena evaluation device of claim 12.

18. The scientific phenomena evaluation device according to claim 4, wherein the lengths of the channels are measured with respect to a direction parallel to a continuous layer liquid flow direction in the channels.

19. The scientific phenomena evaluation device according to claim 2, wherein the plurality of the channels comprises eight channels, and the sectional areas of the channels are different at the fixed ratio with respect to a section area of a channel among the plurality of the channels having a maximum sectional area, wherein the sectional areas of the other seven channels among the plurality of the channels are reduced by the fixed ratio of 10%.

20. The scientific phenomena evaluation device according to claim 19, wherein the channel among the plurality of the channels having the maximum sectional area has a sectional area of 1 mm$^2$, and the sectional areas of the other seven channels among the plurality of the channels are 0.9 mm$^2$, 0.8 mm$^2$, 0.7 mm$^2$, 0.6 mm$^2$, 0.5 mm$^2$, 0.4 mm$^2$, and 0.3 mm$^2$, respectively.

21. The scientific phenomena evaluation device according to claim 2, wherein the sectional areas of the plurality of the channels are different at the fixed ratio with respect to a section area of a channel among the plurality of the channels having a maximum sectional area, wherein the sectional areas of the other channels among the plurality of the channels are reduced by the fixed ratio.

22. A manufacturing method of a scientific phenomena evaluation device, comprising:
forming a first reservoir in a surface of an inverted mold;
forming a plurality of second reservoirs in the surface of the inverted mold around the formed first reservoir;
forming a plurality of channels in the surface of the inverted mold through which the formed first reservoir radially communicates with the formed plurality of the second reservoirs;

applying a resin material to the surface of the inverted mold;

curing the resin material; and releasing the cured resin material from the inverted mold to form a base plate, wherein the formed plurality of the channels have different sectional areas of 1 mm$^2$ or less, and wherein scientific phenomena in the formed plurality of the channels are visually perceivable.

23. The manufacturing method according to claim 22, wherein the forming the plurality of the channels further comprises forming the plurality of the channels such that lengths of the plurality of the channels are equal, and the sectional areas of the channels are different at a fixed ratio.

24. The manufacturing method according to claim 23, the method further comprising:

forming graduations along each of the plurality of the channels, wherein the graduations indicate a diffusion distance.

25. The manufacturing method according to claim 24, the method further comprising:

bonding a cover plate to the surface of the base plate to cover the formed first reservoir, the formed plurality of the second reservoirs, and the formed plurality of the channels, the base plate and/or the cover plate being transparent.

26. The manufacturing method according to claim 25, the method further comprising:

forming through holes in the bonded cover plate that allow communication between the formed first reservoir and the formed plurality of the second reservoirs and outside air.

27. The manufacturing method according to claim 24, wherein the lengths of the plurality of the channels are measured with respect to a direction parallel to a continuous layer liquid flow direction in the plurality of the channels.

28. The manufacturing method according to claim 23, wherein the plurality of the channels comprises eight channels, and the sectional areas of the channels are different at the fixed ratio with respect to a section area of a channel among the plurality of the channels having a maximum sectional area, wherein the sectional areas of the other seven channels among the plurality of the channels are reduced by the fixed ratio of 10%.

29. The manufacturing method according to claim 28, wherein the channel among the plurality of the channels having the maximum sectional area has a sectional area of 1 mm$^2$, and the sectional areas of the other seven channels among the plurality of the channels are 0.9 mm$^2$, 0.8 mm$^2$, 0.7 mm$^2$, 0.6 mm$^2$, 0.5 mm$^2$, 0.4 mm$^2$, and 0.3 mm$^2$, respectively.

30. The manufacturing method according to claim 23, wherein the sectional areas of the plurality of the channels are different at the fixed ratio with respect to a section area of a channel among the plurality of the channels having a maximum sectional area, wherein the sectional areas of the other channels among the plurality of the channels are reduced by the fixed ratio.

31. A manufacturing method of a portable diffusion velocity measurement experimental device for measuring diffusion velocity of a substance, comprising:

forming a first reservoir in a surface of an inverted mold;

forming a plurality of second reservoirs in the surface of the inverted mold around the formed first reservoir;

forming a plurality of channels in the surface of the inverted mold through which the formed first reservoir radially communicates with the formed plurality of the second reservoirs;

applying a resin material to the surface of the inverted mold;

curing the resin material; and releasing the cured resin material from the inverted mold to form a base plate, wherein the formed plurality of the channels have different sectional areas of 1 mm$^2$ or less, and wherein scientific phenomena in the formed plurality of the channels are visually perceivable.

32. The manufacturing method according to claim 31, wherein the forming the plurality of the channels further comprises forming the plurality of the channels such that lengths of the plurality of the channels are equal, and the sectional areas of the channels are different at a fixed ratio.

33. The manufacturing method according to claim 32, the method further comprising:

forming graduations along each of the plurality of the channels, wherein the graduations indicate a diffusion distance.

34. The manufacturing method according to claim 33, the method further comprising:

bonding a cover plate to the surface of the base plate to cover the formed first reservoir, the formed plurality of the second reservoirs, and the formed plurality of the channels, the base elate and/or the cover plate being transparent.

35. The manufacturing method according to claim 34, the method further comprising:

forming through holes in the bonded cover plate that allow communication between the formed first reservoir and the formed plurality of the second reservoirs and outside air.

\* \* \* \* \*